United States Patent [19]
Choi et al.

[11] Patent Number: 6,115,523
[45] Date of Patent: Sep. 5, 2000

[54] PLASTIC OPTICAL FIBER AIRWAY IMAGING SYSTEM

[75] Inventors: Won Young Choi; Dietrich Gravenstein; Samsun Lampotang; Richard Melker; James K. Walker, all of Gainesville, Fla.

[73] Assignee: University of Florida, Gainesville, Fla.

[21] Appl. No.: 08/725,779

[22] Filed: Oct. 4, 1996

[51] Int. Cl.$^7$ .................................................. G02B 6/06
[52] U.S. Cl. ........................ 385/116; 385/117; 600/199
[58] Field of Search .................. 385/116, 117, 385/118; 600/463, 342, 566, 109, 139, 199

[56] References Cited

U.S. PATENT DOCUMENTS

| | | | |
|---|---|---|---|
| D. 410,286 | 5/1999 | Tamirisa | D24/138 |
| 3,417,746 | 12/1968 | Moore et al. . | |
| 3,776,222 | 12/1973 | Smiddy | 600/146 |
| 3,941,121 | 3/1976 | Olinger et al. | 385/117 |
| 4,063,561 | 12/1977 | McKenna | 128/207.15 |
| 4,244,362 | 1/1981 | Anderson | 128/200.26 |
| 4,475,539 | 10/1984 | Konomura | 600/109 |
| 4,567,882 | 2/1986 | Heller | 600/249 |
| 4,617,915 | 10/1986 | Arakawa | 600/131 |
| 4,736,733 | 4/1988 | Adair | 600/109 |
| 4,742,819 | 5/1988 | George | 600/109 |
| 4,846,153 | 7/1989 | Berci | 600/109 |
| 4,854,301 | 8/1989 | Nakajima | 600/102 |
| 4,924,855 | 5/1990 | Salerno et al. | 600/199 |
| 4,943,770 | 7/1990 | Ashley-Rollman et al. | 324/207.17 |
| 4,980,012 | 12/1990 | Nieda et al. | 385/116 |
| 5,125,406 | 6/1992 | Goldstone et al. | 600/380 |
| 5,127,079 | 6/1992 | Suzuki et al. | 385/117 |
| 5,202,795 | 4/1993 | Kashima | 359/645 |
| 5,203,338 | 4/1993 | Jang | 128/662.06 |
| 5,257,636 | 11/1993 | White | 128/897 |
| 5,279,281 | 1/1994 | Harvey | 600/139 |
| 5,327,881 | 7/1994 | Greene | 600/120 |

(List continued on next page.)

FOREIGN PATENT DOCUMENTS

| | | |
|---|---|---|
| 0279576 | 8/1988 | European Pat. Off. . |
| 4132687 | 4/1993 | Germany . |
| 9814112 | 4/1998 | WIPO . |

OTHER PUBLICATIONS

Patil, Vijayalakshmi U., Linda C. Stehling, Howard L. Zauder (1983) Fiberoptic Endoscopy In Anesthesia, pp. 9–35, Year Book Medical Publishers, Inc., Chicago• London. No Month.

*Primary Examiner*—Rodney Bovernick
*Assistant Examiner*—Ellen E. Kang
*Attorney, Agent, or Firm*—Saliwanchik, Lloyd & Saliwanchik

[57] ABSTRACT

The subject invention pertains to a system for imaging the human airway having highly advantageous optical and physical characteristics. In a specific embodiment, the human airway can be imaged during the intubation procedure. The excellent characteristics of the imaging system of the subject invention result, in part, from the use of plastic optic fibers. Plastic fibers are more robust than the glass optical fibers used in currently available imaging systems, and are therefore capable of being bent and/or twisted with less concern of breakage. In addition, the lower costs of plastic fibers enables scopes of the subject invention, in a specific embodiment, to be manufactured for single patient use thereby eliminating the requirement for cleaning, special care, the maintenance of expensive inventory, and most importantly eliminating the opportunity for cross contamination between patients. A further aspect of the subject invention concerns a novel sheath which covers the portion of the imaging system which enters the patient. In this case, the sheath and its optional associated fiber optic illumination is disposable after each use.

4 Claims, 2 Drawing Sheets

U.S. PATENT DOCUMENTS

| | | | |
|---|---|---|---|
| 5,329,940 | 7/1994 | Adair | 128/200.26 |
| 5,337,735 | 8/1994 | Salerno | 600/120 |
| 5,363,838 | 11/1994 | George | 600/194 |
| 5,377,047 | 12/1994 | Broome et al. | 359/654 |
| 5,394,865 | 3/1995 | Salerno | 600/199 |
| 5,402,508 | 3/1995 | O'Rourke et al. | 385/116 |
| 5,431,152 | 7/1995 | Flam et al. | 600/120 |
| 5,445,144 | 8/1995 | Wodicka et al. | 128/207.4 |
| 5,459,605 | 10/1995 | Kempf | 385/34 |
| 5,512,034 | 4/1996 | Finn et al. | 600/138 |
| 5,526,821 | 6/1996 | Jamshidi | 128/753 |
| 5,560,351 | 10/1996 | Gravenstein et al. | 128/200.26 |
| 5,606,170 | 2/1997 | Saaski et al. | 250/458.1 |
| 5,607,386 | 3/1997 | Flam | 600/120 |
| 5,690,117 | 11/1997 | Gilbert | 128/856 |
| 5,733,241 | 3/1998 | King | 600/114 |
| 5,733,242 | 3/1998 | Rayburn et al. | 600/120 |
| 5,735,792 | 4/1998 | Vanden Hoek et al. | 600/138 |
| 5,803,898 | 9/1998 | Bashour | 600/120 |

PLASTIC OPTICAL FIBER AIRWAY IMAGING SYSTEM

The subject invention was made with government support under a research project supported by National Institutes of Health Grant No. 2 R44-GM48277-02. The government has certain rights in this invention.

BACKGROUND OF THE INVENTION

This invention relates to fiber optic scopes and, in a particular embodiment, to intubation scopes. Advantageously, this invention utilizes plastic optical fibers to enhance the safety and efficacy of procedures performed with these novel fiber optic scopes, while simultaneously reducing the costs. Additionally, the scopes of the subject invention can, optionally, utilize a sheath which can reduce the amount of cleaning, i.e., sterilization, required between uses and thereby reduce the costs of use.

It is frequently necessary in medical procedures to insert an endotracheal tube into the trachea of a patient for the purpose of performing diagnostic tests or for the introduction of some means of ventilation, oxygenation, and/or airway protection. Even in the best situations, intubation is often difficult and can give rise to complications. In many patients, establishment of the airway is particularly difficult due to morphologic anomalies such as a large tongue, excessive pharyngeal or laryngeal soft tissue, or tracheal displacement, as well as physiologic events such as laryngospasm, regurgitation of gastric materials, bleeding, or foreign bodies aspiration. These morphologic anomalies and/or events make it difficult to visualize the posterior pharyngeal area and larynx with conventional laryngoscopic maneuvers. In emergency situations, attempts to intubate such patients are difficult and time consuming. Inability to expeditiously intubate the patient and protect the airway can lead to significant hypoxemia, myocardial ischemia, and brain injury. Cases of death have also been related to complications caused by the inability to quickly and clearly see the larynx and trachea.

Proper intubation requires positioning the tip of the tracheal tube within the trachea, midway between the patient's vocal cords and carina. Direct laryngoscopy in many instances is sufficient to intubate the patient, but does not permit the precise confirmation of tip location or tracheal inspection.

If the tracheal tube is not inserted far enough past the vocal cords, the tube may become dislodged and prove to be ineffective in supporting adequate artificial ventilation. Further, the tube may inadvertently end up in the esophagus. Esophageal intubations, resulting from either dislodgement or incorrect initial placement have led to severe morbidity and even death. At the other extreme, if inserted too far and beyond the carina, the tube may only permit ventilation of one lung (as opposed to both lungs). Thus, correct tube placement is essential in order to properly ventilate the patient.

Even the most skilled anesthesiologist may encounter what is commonly referred to as a "difficult" airway. This occurs in about 5% of all operating room intubations, with an even higher incidence of an inability to fully visualize the glottic opening. The incidence level is significantly higher in other areas of the hospital and prehospital environment. Although presurgical examination of the jaw, teeth, mouth opening and neck motion assists in gauging the degree of difficulty likely to be encountered at intubation, not all difficult intubations can be identified in advance. There is always the unexpected difficult airway, discovered only at the time of intubation. In emergency situations, there is little if any time to perform an airway assessment prior to attempting intubation. Thus, all emergency intubations are considered "difficult" intubations.

There are a number of techniques used to assist in difficult intubations. These include laryngoscopy, with or without axial cervical traction, fiberoptic bronchoscopy, with or without a transtracheal retrograde wire guide, blind nasal and the lighted stylet techniques.

Fiberoptic bronchoscopy is considered by many as the "gold standard" for viewing the airway and properly positioning a tracheal tube. The complexity of operating and cost of buying, maintaining, cleaning, and replacing existing glass fiberoptic systems, which are fragile, are major factors preventing greater usage of bronchoscopy.

The retrograde wire technique involves placing a needle into the cricothyroid space and advancing a guide wire through the needle and upward through the glottic opening between the vocal cords and pharynx until it emerges from the nose or mouth. After the wire is localized, a fiberoptic bronchoscope or tracheal tube is advanced over the wire into the larynx. This technique is not recommended in emergency situations. Major negative concerns associated with this technique are its invasive nature and the risk for bleeding and infection in the trachea. The wire can also cause injury to the tracheal tissue and/or vocal cords.

A lighted stylet incorporates aspects of both the fiber scope and retrograde wire techniques. It is essentially a standard stylet with a bright light at the distal end. This technique provides only indirect transcutaneous illumination of the trachea. Direct visualization is not possible when using a lighted stylet.

Fiberoptic intubating scopes with cameras and/or eyepieces for viewing that which is illuminated by the fiber optic system have previously been described. See, for example, U.S. Pat. Nos. 3,776,222; 4,742,819; and 5,363,838. Current fiber optic scopes, for example, intubation scopes and associated systems for imaging the human airways, typically use glass optical fibers. Unfortunately, these intubation scopes and associated systems utilizing glass optic fibers are expensive to purchase, clean, and store. Additionally, the glass optical fibers within these scopes are prone to breaking thereby shortening the life of the scopes.

BRIEF SUMMARY OF THE INVENTION

The subject invention pertains to a system for imaging the human airway having highly advantageous optical and physical characteristics. The excellent characteristics of the imaging system of the subject invention result, in part, from the use of plastic optical fibers. Plastic fibers are more robust than the glass optical fibers used in currently available imaging systems, and are therefore capable of being bent and/or twisted with less concern of breakage. In addition, the lower costs of plastic fibers enables scopes of the subject invention, in a specific embodiment, to be manufactured for single patient use thereby eliminating the requirement for cleaning, special care, the maintenance of expensive inventory, and most importantly eliminating the opportunity for cross contamination between patients. A further aspect of the subject invention concerns a novel sheath which can cover all or a portion of the parts of the imaging system which enter the patient. This sheath can reduce the need for expensive sterilization of the subject intubation scope after use.

The imaging system of the subject invention is highly advantageous because of its longer life, increased ruggedness, greater flexibility, good image quality, optional disposability, and lower cost. These scopes are useful, for example, for observing the bronchi of the lungs, locating the tracheal opening to allow insertion of an endotracheal tube into the trachea for intubation, and visually locating the endotracheal tube tip. Specifically, using a scope of the subject invention, a practitioner can easily and precisely identify the exact location of the distal end of the tracheal tube, as well as the various anatomical airway landmarks. Currently, this degree of precision is only possible with an expensive glass fiberoptic bronchoscope. In addition, the scopes of this invention are particularly advantageous for use in anesthesiology.

In a specific embodiment, the subject invention pertains to a plastic optical fiber imaging scope, having an optional sheath, for intubation. This intubation scope can be used for intubation of patients under general and/or local anesthesia. The intubation scope of this embodiment can be disposable, sterilizable for reuse, or enclosed within a disposable sheath for reuse without expensive sterilization. Due to lower cost for the plastic optical fiber scopes, the scopes of the subject invention are particularly advantageous for situations calling for disposable scopes, and can be less expensive than the cleaning and sterilization costs for existing glass scopes.

Imaging scopes with varying components and corresponding performance capabilities can be manufactured with this new technology. By way of these multiple embodiments, the subject invention can be used for imaging essentially all of the airway system of humans and animals.

DETAILED DISCLOSURE OF THE INVENTION

Figure 1:
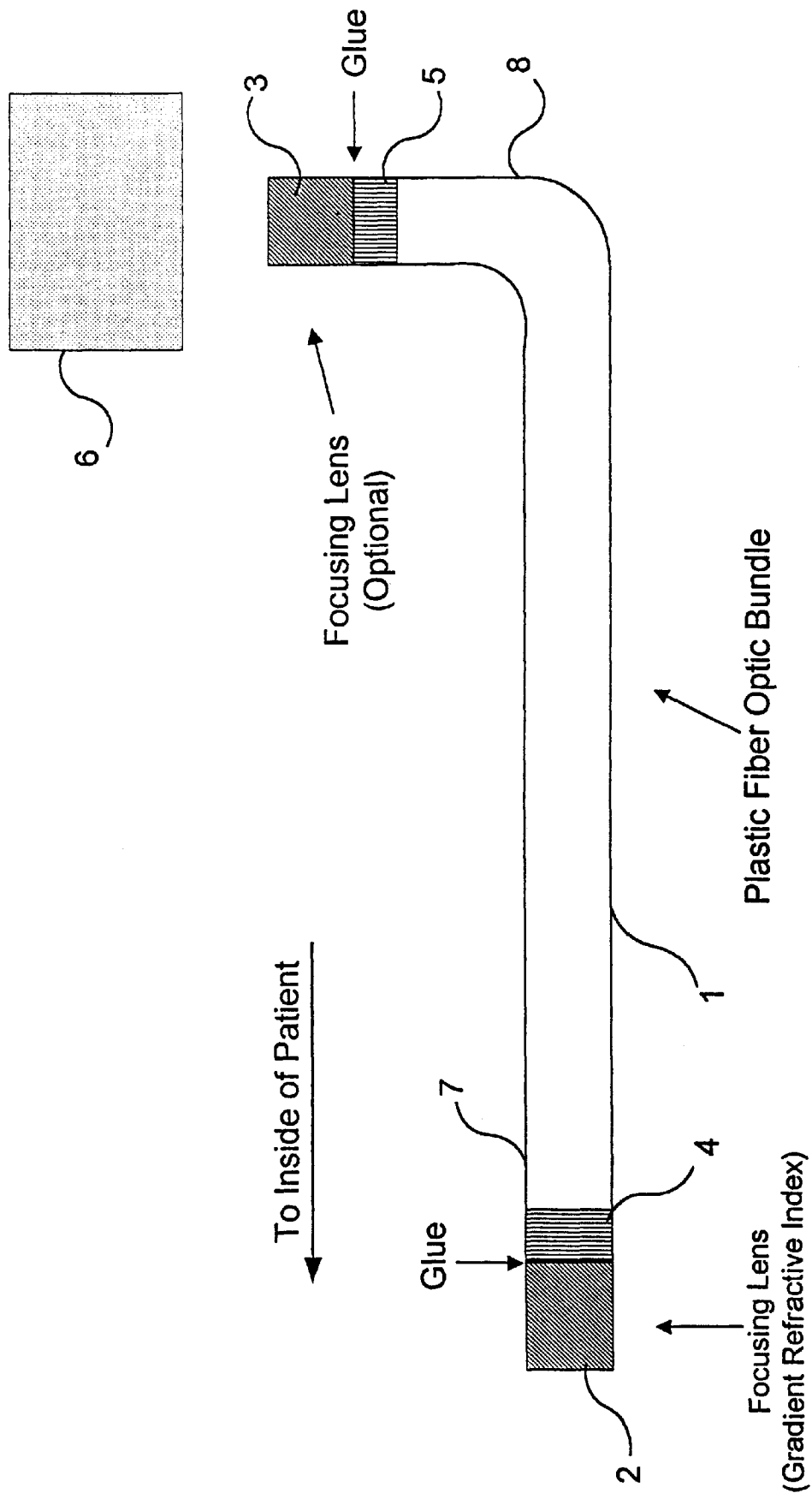
FIG. 1 shows an embodiment of the intubation scope of the subject invention.

The subject invention utilizes plastic optical fiber to produce fiber optic scopes, and in a particular embodiment, intubation scopes, for use in imaging the human airway. The device of the subject invention can assist practitioners in properly introducing and confirming the position of tracheal tubes. Although the device has application in "difficult" intubations, use in all intubations is envisioned for confirming optimal tracheal tube advancement between the vocal cords and positioning within the trachea. This can only be achieved with direct tracheal visualization. The plastic fiberoptic device of the subject invention makes this possible while also being highly cost effective.

The device of the subject invention has application for intubating patients undergoing general, intravenous and local anesthesia and in emergency situations. Thus, the device can be used in surgical procedures as well as in intensive care units, emergency departments and the pre-hospital settings.

The device of the subject invention incorporates plastic fiberoptic technologies, enabling direct visualization of the pharynx, glottic opening, larynx and trachea and thus, facilitates accurate tracheal tube placement and periodic verification of tracheal tube tip location. Further, the device can easily be steered, simplifying proper tube placement. Traditional reusable glass fiber bronchoscope are expensive to purchase and maintain. Effectively cleaning the bronchoscope is difficult. It is also recognized that sterility of existing reusable glass fiber bronchoscopes is often not achieved after use with a patient.

The subject invention achieves substantial improvements in performance compared to existing glass fiber scopes, including: (1) longer life; (2) increased ruggedness; (3) greater flexibility; (4) optional disposability, and (5) less expense. By varying the components of the intubation scopes utilizing the teachings of the subject invention, these performance characteristics can be optimized, to facilitate the use of these scopes for imaging a vast portion of the human airways and in a variety of situations. Thus, the scopes of the subject invention can be used, for example, for observing the bronchi of the lungs, locating the tracheal opening to allow insertion of an endotracheal tube into the trachea for intubation, and locating the endotracheal tube tip. In particular, an anesthesiologist can, using the scope of the subject invention, stand behind the head of a patient while performing an intubation. Additionally, this device will reduce the force necessary for normal laryngoscopy. Reduced force leads to less tissue trauma, hemodynamic changes, and post-operative sore throat complications. Advantageously, the scopes of the subject invention are more cost effective in situations requiring a disposable scope and/or can be used with an optional disposable sheath to enclose the portion of the scope entering the body to reduce cleaning and sterilization costs.

In one embodiment the light source can be derived from a standard laryngoscope. In a second embodiment, one or more optical fiber(s) can transmit the light required to illuminate the airway. The source of the light can be, for example, a modified laryngoscope handle or an inexpensive separate light source.

Image guides used in conjunction with intubation, for example, bronchoscopes, are typically made with step index glass optical fiber. Plastic optical fiber can also be fabricated with a step index of refraction. Both plastic and glass step index fibers are constructed with a core of refractive index $n_1$, and a cladding of refractive index $n_2$, where $n_1 > n_2$. A second type of fiber is known as gradient index or graded index fiber and can also be made with plastic or glass. Since flexibility is an important characteristic for the scopes of the subject invention, plastic gradient index optical fibers are preferred over glass gradient index optical fibers for the subject image guides.

In comparing the step index structure with the gradient index structure, it is noted that there are different trajectories of light rays in these two fiber structures. Within step index fiber, the light travels in straight lines, and is reflected at the core-cladding interface. While in gradient index fiber, the light travels in a curved trajectory always being refracted back towards the axis of the fiber. As a consequence, an image can be conveyed within a single gradient index fiber, while an image cannot be conveyed within a single step index fiber. Although, when conveying an image in a single gradient index fiber, some correction may be required to correct aberrations in the output image, for example, by using one or more negative gradient index lens attached to one or both ends of the single gradient index fiber.

Referring to FIG. 1, the intubation scope of the subject invention comprises an image guide 1, which conveys optical images from inside the body, for example from inside the human airways, to outside of the body for viewing by a medical caregiver. In a specific embodiment, this image guide 1 can comprise a single gradient index plastic optical fiber. In a specific embodiment, this single fiber can have a diameter, for example, of about 0.5 to 2.0 mm. A focusing lens 2 can optionally be used to focus the desired image into the distal tip 7 of the single fiber, the distal tip 7 entering the body, generally through the mouth or nose. This lens 2 can be attached by, for example, optical glue, and can act as a bi-convex lens to focus the desired image onto the distal tip of the single fiber. In this single fiber embodiment, a negative gradient rod lens, made of glass or plastic, can be attached to the proximal end of the single fiber image guide 1 and used to correct for aberrations resulting from the use of a single gradient index plastic optical fiber to carry the image.

In an alternative embodiment, this image guide 1 can comprise a bundle of plastic optical fibers. This plastic fiber optic image guide 1 can be made of a plurality of individual plastic optical fibers which have been fused together. In a specific embodiment, this bundle can comprise approximately 10,000 individual plastic optical fibers, wherein the bundle is approximately 1.0 millimeter in diameter. This bundle can comprise gradient index plastic optic fibers and, in a preferred embodiment, this bundle can comprise step-index plastic optical fibers. Each end of the bundle can be polished to allow high resolution imaging. A focusing lens 2 can be used to focus the desired image onto the distal tip 7 of the bundle, the distal tip 7 entering the human body, generally through the mouth or nose. This lens 2 can be attached at the distal tip 7 of the bundle, for example, by optical glue 4. This lens 2 can act like a bi-convex lens to focus the image onto the distal tip of the fiber optic bundle. In a preferred embodiment, the lens 2 can be a gradient-index glass rod lens. In a more preferred embodiment, the lens 2 can be a gradient-index plastic rod lens.

An optical system can transmit the image from the proximal end of the fiberoptic image guide 1 onto a charge coupled device (CCD). The CCD can be used to convert the image into an electrical signal which can be displayed on a monitor. Alternatively, camera equipment available to the physician can be used. In a specific embodiment, the proximal tip 8 of the image guide 1 is arranged so that the image from inside the patient is focused directly onto an imaging eyepiece 6. The imaging eyepiece 6 can be connected to a camera for viewing the image, or the image can be viewed directly by the medical caregiver through the imaging eyepiece 6.

In an alternative embodiment, when a camera is not to be used for viewing the image, a second lens 3 can be attached, for example, by optical glue 5, to the proximal tip 8 of the image guide 1, the proximal tip remaining outside of the body. This lens can be, for example, a mini plastic lens microscope connected directly to the proximal end of the fiber scope for direct viewing by the caregiver, i.e., by placing an eye to the microscope lens. In a specific embodiment, the fiberoptic image guide can be lengthened and mini plastic lens microscope can be mounted on a caregiver's head, for example, by a mounting means such as a pair of glasses or goggles. This allows the caregiver to have both hands free to perform, for example, an intubation, while being able to view the patient and the image from the scope without having to turn his or her head.

Manufacturing the subject invention without a camera can be done to reduce costs or to meet the needs of certain medical situations. However, when the eyepiece is connected to a camera, the image can be displayed via, for example, a television monitor. This monitor can be, for example, placed out of the sterile field for viewing.

In a specific embodiment, the visualization system scope of the subject invention can be inserted into a plastic tube (sheath), which can have a transparent end plate. This combination can then be used for imaging the airway. The image viewed through the end plate is unimpaired by the sheath or end plate. The advantage of this sheath is that it is disposable and allows the intubation scope to be reused with minimal sterilization.

In a preferred embodiment, the sheath can have at least one internal, or external, illuminating optical fiber(s) which transmits light to illuminate the internal body structure to be imaged. Additionally, it is preferred but not essential, that there be no transparent end plate at the distal end of the illuminating optical fiber(s) to avoid the illuminating light reflecting at such a plate and impairing the quality of the image. A longitudinal cross section and a transverse cross section of a sheath comprising an external illumination fiber are shown in FIGS. 2B and 2E, respectively.

When performing, for example, an intubation, a flexible stylet, typically made of metal, is often used in conjunction with an endotracheal tube to facilitate the insertion of the tube into the body. In a specific embodiment, the intubation scope can incorporate a stylet, wherein the stylet can be bent into the shape which the caregiver believes will facilitate the easiest and safest insertion of the endotracheal tube, and then the endotracheal tube, which typically surrounds the stylet and scope, can be inserted into the patient. A longitudinal cross section and a transverse cross section of a sheath comprising an external illumination fiber, where the sheath is designed to fit over a stylet incorporated with a plastic optical fiber image guide, are shown in FIGS. 2C and 2E, respectively. In this case, the sheath and illuminating fiber could be regarded as disposable after a single use.

Accordingly, the intubation scope and/or sheath of the subject invention can comprise such a stylet, such that many combinations of scope, stylet, illuminating fiber(s), and sheath are possible.

The intubation scope and method of tracheal tube placement verification of the subject invention represents a significant cost saving for the hospital. Rather than having to periodically x-ray the patient to verify tube position, the hospital staff can use the subject invention to not only confirm proper tube placement but to also evaluate the airway for obstruction and/or erosion, which is not possible with x-rays.

The device of the subject invention is easily connected to bronchoscope imaging equipment, without incurring the cost of buying and sterilization processing of the bronchoscope. In another embodiment, an off the shelf LCD device similar to a Sony "WATCHMAN" can be utilized for imaging.

Following are examples which illustrate procedures for practicing the invention. These examples should not be construed as limiting.

EXAMPLE 1

The device of the subject invention not only makes intubation easier and more accurate, but also reduces the potential for inflicting injury with the laryngoscope blade. Using the device of the subject invention, the practitioner only needs to use the laryngoscope blade to control the position of the patients tongue. The device can also be used without a laryngoscope and for nasotracheal intubation.

The device of the subject invention can comprise a bundle of 10,000 individual plastic optical fibers (bundle is approximately 1.0 millimeter in diameter). The resolution of the image is equivalent to an existing glass fiberoptic bronchoscope, providing good visualization of the patient's airway.

The manufacturing process places the bundle integral to a standard malleable stylet. An additional fiber may be used for illuminating purposes. Suctioning and insufflation can be added by adding an additional channel if desired.

A focusing lens (i.e., gradient refractive index lens) is placed at the distal tip of the optical fibers and acts like a bi-convex lens to focus the image onto the distal tip of the fiber optic bundle. An optical system transmits the image from the proximal end of the fiberoptic bundle onto a charge coupled device (CCD). The CCD is used to convert the image onto the tip of an electrical signal which can be displayed on a monitor. Alternatively, camera equipment available to the physician may be used.

EXAMPLE 2

Figure 2D:
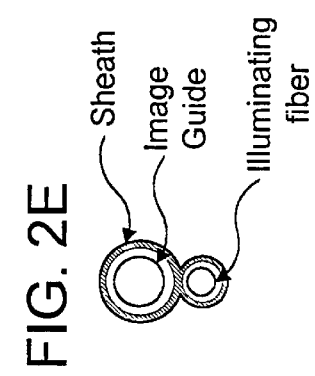
FIGS. 2A and 2D illustrate a longitudinal cross section and a transverse cross section, respectively, of the distal end of a sheath designed to fit over a plastic optical fiber image guide.
Figure 2E:
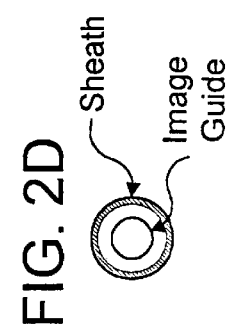
FIGS. 2B and 2E illustrate a longitudinal cross section and a transverse cross section, respectively, of the distal end of a sheath designed to fit over a plastic optical fiber image guide, wherein the sheath comprises an illumination fiber.
Figure 2F:
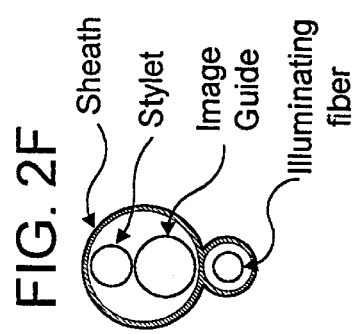
FIGS. 2C and 2F illustrate a longitudinal cross section and a transverse cross section, respectively, of the distal end of a sheath designed to fit over a stylet incorporated with a plastic optical fiber image guide, wherein the sheath comprises an illumination fiber.
Figure 2A:
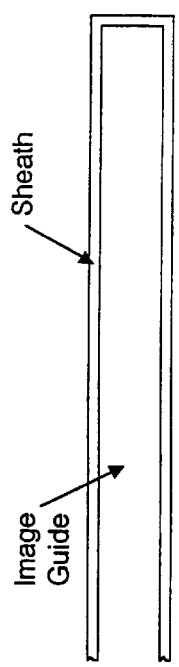
Figure 2B:
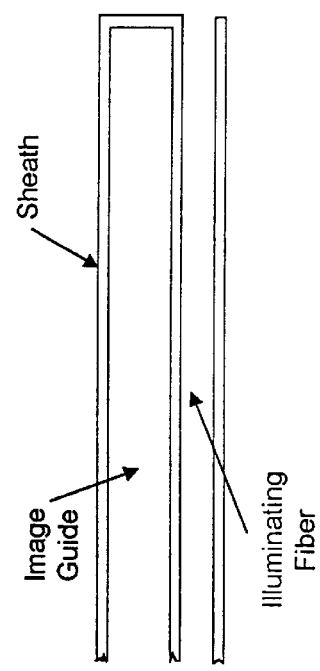
Figure 2C:
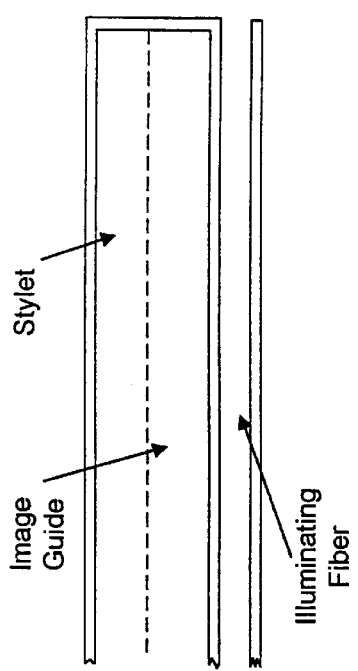

Referring to FIGS. 2A, 2B, 2C, 2D, 2E, and 2F, this example provides three illustrative combinations of image guide, illuminating fiber, stylet, and/or sheath. FIGS. 2A and 2D illustrate a longitudinal cross section and a transverse cross section, respectively, of the distal end of a sheath designed to fit over a plastic optical fiber image guide. The sheath covers the distal tip of the image guide with a transparent end plate. In this case, any illuminating fibers and/or stylets would not be enclosed within this sheath, although they could have their own sheaths.

FIGS. 2B and 2E illustrate a longitudinal cross section and a transverse cross section, respectively, of the distal end of a sheath designed to fit over a plastic optical fiber image guide, wherein the sheath comprises an illumination fiber. The distal end of the illumination fiber is not covered by the sheath, in this example, so as to not impair the image. Accordingly, the illuminating fiber can be disposed of with the sheath. In this embodiment, the sheath acts to attach and position the illumination fiber with respect to the image guide.

FIGS. 2C and 2F illustrate a longitudinal cross section and a transverse cross section, respectively, of the distal end of a sheath designed to fit over a stylet incorporated with a plastic optical fiber image guide, wherein the sheath comprises an illumination fiber. The distal end of the illumination fiber is not covered by the sheath, but the distal end of the image guide plus stylet is covered. In this embodiment, the stylet can be reused along with the image guide. Other geometrical arrangements of the stylet, image guide, and illumination fiber are obviously possible.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method of positioning an endotracheal tube in a patient, said method comprising the steps of:

(a) inserting an intubation scope into an endotracheal tube to form an intubation scope-endotracheal tube combination, said intubation scope comprising an image guide and a stylet wherein said stylet retains its shape when bent, wherein the tube and scope combination can be bent into a shape, which facilitates placement into a patient, such that the tube and scope combination retains such shape due to the stiffness of the stylet;

(b) observing an image from a distal tip of said intubation scope wherein said image is transmitted by said image guide; and (c) guiding said scope-tube combination into the patient, wherein observing the image from the distal tip of said intubation scope facilitates the positioning of said endotracheal tube.

2. The method, according to claim 1, further comprising the step of bending the scope-tube combination into a shape which facilitates guiding of the scope-tube combination into said patient.

3. A method of positioning an endotracheal tube in a patient, said method comprising the steps of:

(a) inserting an intubation scope into an endotracheal tube to form an intubation scope-endotracheal tube combination, said intubation scope comprising an image guide and a means for retaining the shape of the scope when bent, wherein the tube and scope combination can be bent into a shape, which facilitates placement into a patient, such that the tube and scope combination retains such shape due to the stiffness of the means for retaining the shape of the scope when bent;

(b) observing an image from a distal tip of said intubation scope wherein said image is transmitted by said image guide; and (c) guiding said scope-tube combination into the patient, wherein observing the image from the distal tip of said intubation scope facilitates the positioning of said endotracheal tube.

4. The method, according to claim 3, further comprising the step of bending the scope-tube combination into a shape which facilitates guiding of the scope-tube combination into said patient.

* * * * *

UNITED STATES PATENT AND TRADEMARK OFFICE
CERTIFICATE OF CORRECTION

PATENT NO. : 6,115,523
DATED : September 5, 2000
INVENTOR(S) : Choi et al.

It is certified that error appears in the above-identified patent and that said Letters Patent is hereby corrected as shown below:

Inventors,
Please strike the following first and last named inventors "Won Young Choi" and "James K. Walker".

Signed and Sealed this

Seventeenth Day of July, 2001

*Attest:*

*Attesting Officer*

NICHOLAS P. GODICI
*Acting Director of the United States Patent and Trademark Office*